United States Patent [19]
Rubinstein

[11] Patent Number: 4,556,558
[45] Date of Patent: * Dec. 3, 1985

[54] TREATMENT OF FACTOR VIII CONCENTRATE TO MINIMIZE THE AFFECT OF UNDESIRABLE MICROORGANISMS

[75] Inventor: Alan Rubinstein, Beverly Hills, Calif.

[73] Assignee: Cedars-Sinai Medical Center, Los Angeles, Calif.

[*] Notice: The portion of the term of this patent subsequent to Jun. 26, 2001 has been disclaimed.

[21] Appl. No.: 624,992

[22] Filed: Jun. 26, 1984

Related U.S. Application Data

[63] Continuation of Ser. No. 499,489, May 31, 1983, abandoned, which is a continuation-in-part of Ser. No. 377,863, May 13, 1982, Pat. No. 4,456,590, which is a continuation-in-part of Ser. No. 317,513, Nov. 2, 1981, abandoned, which is a continuation of Ser. No. 205,913, Nov. 12, 1980, abandoned.

[51] Int. Cl.$^4$ ............................................. A61K 35/16
[52] U.S. Cl. .................................................... 424/101
[58] Field of Search ......................................... 424/101

[56] References Cited

U.S. PATENT DOCUMENTS

| | | |
|---|---|---|
| 3,041,242 | 6/1962 | Barr et al. |
| 3,100,737 | 8/1963 | Auerswald et al. |
| 3,859,168 | 1/1975 | Barth et al. |
| 4,250,139 | 2/1981 | Luck et al. |
| 4,297,344 | 10/1981 | Schwinn et al. |
| 4,327,086 | 4/1982 | Fukishima et al. |
| 4,347,259 | 8/1982 | Suzuki et al. |
| 4,495,278 | 1/1985 | Thomas ................................ 424/101 |

FOREIGN PATENT DOCUMENTS 1471336  4/1977  United Kingdom .

OTHER PUBLICATIONS

Kaplan, "The Heat Inactivation of Vaccinia Virus," *J. Gen. Microbiol.*, 18:58–63, (1958).
Cowdery et al., "Stability Characteristics of Freeze-Dried Human Live Virus Vaccines," *Develop. Biol. Standard*, 36:297–303.
Beardmore et al., "Preservation of Influenza Virus Infectivity by Lyophilization," *Applied Microbiology*, 16(2):362–365, (1968).
Greiff et al., "Stability of Suspensions of Influenza Virus Dried to Different Contents of Residual Moisture by Sublimation in Vacuo," *Applied Microbiology*, 16(6):835–840, (1968).
Plowright et al., "Studies on Rinderpest Culture Vaccine. III. Stability of the Lyophilized Product," *Res. Vet. Sci.*, 11:71–81, (1970).
Apostolov et al., "Selective Inactivation of the Infectivity of Freeze-Dried Sendai Virus by Heat," *Cytobiology*, 10:255–259, (1973).
Schable et al., "Stability of a Reference Panel of Lyophilized Hepatitis B Antigens and Antibodies," *J. Biol. Standardization*, 7:293–299, (1979).
Berge et al., "Preservation of Enteroviruses by Freeze-Drying," *Applied Microbiology*, 22(5):850–853, (1971).
Grieff et al., "An Accelerated Storage Test for Predicting the Stability of Suspensions of Measles Virus Dried by Sublimation in Vacuo," *J. Immunology*, 94(3):395–400, (1965).
Kraft et al., "Lyophilization of Poliomyelitis Virus. Heat Inactivation of Dry MEFL Virus," *Proc. Soc. Exp. Biol. Med.*, 9:306–309, (1954).
Scatchart et al., "Chemical, Clinical, and Immunological Studies on the Products of Human Plasma Fractionation. IV. A Study of the Thermal Stability of Human Serum Albumin," *J. Clin. Invest.*, 23:445–453, (1944).
Sirridge, *Laboratory Evaluation of Hemostatis*, Second Edition, Lea & Febiger, Philadelphia, 1974, pp. 7–8.
Bangham et al., "Stability of Some Clotting Factors in Freeze–Dried Factor VIII–Reference Plasma and Concentrate," *Chem. Abstracts*, 76:22760u, (1972).
Brozovic et al., "Stability of Prothrombin and Factor VII in Freeze–Dried Plasma," *J. Clin. Path.*, 24:690–693, (1971).
Plasma Products: Use and Management. A Technical Workshop, Kolins et al. (Eds.), The Committee on Technical Workshops, American Association of Blood Banks, Anaheim, CA, (1982).
Gerety et al., "Plasma Derivatives and Viral Hepatitis," *Transfusion*, 22(5):347, (1982).
Tabor et al., *Infectious Complications of Blood Transfusion*, Academic Press, New York, 1982, pp. 6, 24.
Aronson et al., "Historical and Future Therapeutic Plasma Derivatives (Epilogue)," *Seminars in Thombosis and Hemostasis*, VI(2):121–123, (1980).
Rosenberg et al., "Thermoinactivation of Virus of Botkin's Disease (Hepatite Virus) in Dry Fibrinogen and Albumin Preparations," *XII International Congress on Blood Transfusion Abstracts*, MIR Publishers, Moscow, 1969, pp. 473–475.
Soulier et al., "Prevention of Virus B Hepatitis (SH Hepatitis)," *Amer. J. Dis. Child*, 123:429–434, (1972).
Paine et al., "Human Albumin Infusions and Homologous Serum Jaundice," *JAMA*, 150(3):199–202, (1952).
Havens et al., "Properties of the Etiologic Agent of Infectious Hepatitis," *Proc. Soc. Exp. Biol. Med.*, 58:203–204, (1945).
Bertrand et al., "Clinical Investigations with a Heat-Treated Plasma Protein Fraction—Plasmanate," *Vox Sang.*, 4385–402, (1959).

(List continued on next page.)

*Primary Examiner*—Sam Rosen
*Attorney, Agent, or Firm*—Lyon & Lyon

[57] ABSTRACT

The invention is directed to treating blood clotting Factor VIII products to minimize the presence of undesirable microorganisms involving process steps of drying and heating of the product. In addition the invention is directed to products obtained by the process.

12 Claims, No Drawings

OTHER PUBLICATIONS

Roberts et al., "Post-Transfusion Hepatitis Following the Use of Prothrombin Complex Concentrates," *Thrombos, Diathes, Haemorrh.,* (Stuttg.), 33:610–616, (1975).

Tabor et al., "Removal of Hepatitis-B-Virus Infectivity from Factor-IX Complex by Hepatitis-B Immune--Globulin," *The Lancet,* pp. 68–70, Jul. 12, 1980.

Allen et al., "Homologous Serum Jaundice and its Relation of Methods of Plasma Storage," *JAMA,* 144(13):1069–1074, Nov. 25, 1950.

Funakoshi et al., "Injectable Inactivated Vaccine Against Hepatitis B," *Chem. Abstracts,* 89:65254t, (1978).

Schwinn et al., "Blood Coagulation Factors," *Chem. Abstracts,* 94:36335t, (1981).

Thomas, Baxter-Travenol, pp. 1–6, 10/29/79.

Bidwell, *The Purification of Bovine,* Antihemophilic Globulin, *Br. J. Hematol.,* 1:35–45, (1955).

Podolsky et al, Improved Method of Lyophilic Dessication of Glucose Stabilized Plasma, Problems of Hemotology and Blood Transfusion, (1967).

Spaet et al, Prophies of Bovine Anti Hemophilic Factor, Bovine Anti Hemophilic Factor, (1953).

MacFarlane et al, The Use of Animal Antiheomophlin Globulin and Human Plasma in Thirteen Cases, *Lancet,* (1957).

Thelin et al, Sedimentation of Plasma AntiHemophilic Factor, *Archives of Biochemistry and Biophesis,* 95, 70–76, (1961).

TREATMENT OF FACTOR VIII CONCENTRATE TO MINIMIZE THE AFFECT OF UNDESIRABLE MICROORGANISMS

RELATED APPLICATIONS

This is a continuation of Ser. No. 499,489 filed on May 31, 1983, now abandoned, which is a continuation-in-part of application Ser. No. 377,863 filed on May 13, 1982 which is now U.S. Pat. No. 4,456,590, which is in turn a continuation-in-part of application Ser. No. 317,513 filed Nov. 2, 1981, now abandoned, which is in turn a continuation of application Ser. No. 205,913 filed Nov. 12, 1980, now abandoned, the entire disclosure of which is incorporated herein by reference.

TECHNICAL FIELD

The present invention relates generally to methods for heat treating plasma fractions and is particularly directed to a series of steps whereby Factor VIII concentrate may be heated in lyophilized form for the purpose of inactivating undesirable microorganisms present therein.

BACKGROUND ART

Clotting factor concentrates obtained from fractionated blood plasma have heretofore been utilized to intervene therapeutically with respect to patients suffering from hemophilia and other inherited bleeding disorders. Unfortunately, the otherwise salutary effects of clotting factor concentrates on the hemophiliac patient tend to be compromised as a consequence of the inordinate risk posed to the patient by the presence of hepatitis virus or other undesirable microorganisms in the concentrates. For example, commercial Factor VIII and IX concentrates are typically employed to increase the clotting ability of a hemophilia victim's blood, but these concentrates are prepared from pools of plasma contributed by thousands of donors and contain the inherent hepatitis risk of a like number of single unit transfusions. As McCullen and Zuckerman have shown, see *Journal of Medical Virology*, Vol. 8, No. 29 (1981), despite strigent screening of individual donors for hepatitis B surface antigens (HBsAg), such plasma pools clearly transmit both hepatitis B and non-A, non-B hepatitis.

Hepatitis transmission by albumin and other heat-stable plasma components unrelated to blood coagulation has heretofore been prevented by heating the plasma components in solution at temperatures of 60° C. for ten hours. Similar attempts to heat clotting factor concentrates in solution, by way of contrast, have been shown to markedly reduce or eliminate clotting factor activity in the concentrates and thus do not appear to offer a viable solution to the problem of hepatitis transmission associated with conventional hemophiliac therapy. More recently, highly purified Factor VIII precipitate has been dissolved in a solution of sucrose glycine and heated for ten hours at 60° C. Although the Factor VIII concentrate subsequently derived from the heated precipitate does retain clotting factor activity, the yields obtained using this approach are very low, e.g., about 8%. See Heimburger, et al., *Hemostasis*, Vol. 10 (supplement 1), p. 204 (1981) and Heimburger, et al., *Blut*, Vol. 44, p. 249-251 (1982). As a net result, the prior art to date does not furnish any means for effectively inactivating hepatitis virus present in clotting factor concentrates nor does the prior art teach a means for preventing the transmission of hepatitis virus to patients undergoing therapy with clotting factor concentrates.

DISCLOSURE OF THE INVENTION

It is therefore an object of the present invention to provide a method for heat treating clotting factor concentrates to inactivate any undesirable microorganisms present therein without reducing clotting factor activity.

It is another object of the present invention to provide a method for heat treating Factor VIII concentrates to inactivate any hepatitis virus present therein, which method results in substantial yields of concentrate without significant reduction of clotting factor activity in the concentrate.

It is still another object of the present invention to provide a method for heat treating Factor VIII concentrates wherein the concentrates are first prepared in lyophilized form to enhance the stability of the concentrates during the heating process.

It is a further object of the present invention to provide a method for heat treating lyophilized plasma fractions to produce a vaccine effective against both hepatitis B virus and non-A, non-B hepatitis virus.

These and other objects of the present invention are achieved by lyophilizing either whole plasma or plasma fractions such as Factor VIII concentrate, Factor IX concentrate, fibrinogen and cryoprecipitate and thereafter subjecting the lyophilized whole plasma or plasma fractions to elevated temperatures for varying periods of time.

BEST MODE FOR CARRYING OUT THE INVENTION

The ability to isolate clotting factors present in human blood has been indispensable in understanding the pathology of hemophilia and other inherited bleeding disorders. Concomitantly, the discovery of plasma fractionation schemes for obtaining practical quantities of clotting factor concentrates has enabled medical science to utilize the clotting factor concentrates as therapeutic tools in treating bleeding disorders. Transfusion therapy employing Factor VIII and Factor IX concentrates in particular has proven quite successful in ministering to hemophiliac patients. Unfortunately, the risk of hepatitis transmission due to the large number of plasma donors required for commercial production of clotting factor concentrates remains as the one serious drawback associated with transfusion therapy. A typical plasma fractionation scheme, disclosed in *Seminars in Thrombosis and Hemostasis*, Vol. VI, No. 1, p. 4 (1979), yields cryoprecipitate and supernate, the former fraction constituting a source of both Factor VIII concentrate and fibrinogen and the latter fraction constituting a source of Factor IX concentrate in addition to Factors II, VII, and X concentrates. As Gerety and Eyster have demonstrated in "Hepatitis Among Hemophiliacs", *Non-A, Non-B Hepatitis*, p. 103-106 (1981), hepatitis B virus initially present in whole plasma is distributed to the Factor VIII and Factor IX derivatives during the plasma fractionation process. As also demonstrated by Maynard and Bradley, "Transmission by Blood Products", *Non-A, Non-B Hepatitis*, p. 78-79 (1981), non-A, non-B hepatitis exists in both Factor VIII and Factor IX derivatives. Previous attempts to heat-treat clotting factor concentrates in solution for the purpose of inactivating hepatitis virus have been ineffective. The development of techniques for lyophilizing clotting factor derivatives, however, has opened a new avenue of exploration with regard to stabilizing clotting factor derivatives during the heat treating process, in turn establishing a means for inactivating hepatitis virus present in the clotting factor derivatives without destroying clotting factor activity.

TEST PROCEDURES FOR VERIFYING RETENTION OF CLOTTING FACTOR ACTIVITY

Paired samples of various lyophilized plasma fractions, each such pair having identical lot numbers, were received from several manufacturers. The samples generally weighed less than 100 g and were packaged in vials having volumes of 60 ml to 90 ml. One sample in each pair was heated, either by placing the sample vial in a water bath or dry oven at a predetermined temperature under room pressure for a predetermined period of time, or by placing the lyophilized material itself in a dry oven without the vial present. The remaining sample in each pair served as a control and was refrigerated at 4°–6° C. during the heat-treating process. Following heat treatment, both the control and heat-treated lyophilized samples were reconstituted with sterile water. Reconstitution was generally carried out according to manufacturer's specifications, although the solubility of some heat-treated samples was markedly improved by increasing the amount of sterile water used during reconstitution over that recommended by the manufacturer. In vitro Factor VIII and Factor IX assays were performed using a one-stage manual fibrometer method at dilutions ranging between 1:40 and 1:400 to obtain a measure of Factor VIII and Factor IX clotting activity. In vitro recovery of fibrinogen following reconstitution of both the control and heat-treated lyophilized fibrinogen samples was measured in a similar fashion. In some of the experiments, reconstituted plasma fractions were observed for light transmission at 580 nm in a Beckman Model 25 Spectrophotometer. Agarose gel electrophoresis with an ICL immunoelectrophoresis plate was carried out for several of the Factor VIII and Factor IX paired samples, using goat anti-human serum supplied by Hyland Diagnostics as a standard. The plates were specifically electrophoresed by a Buchler power supply set at 25 ma for 35 minutes. Upon completion of the electrophoresis, the plates were incubated in antisera for 18 to 24 hours and examined under indirect light. Panagell electrophoresis with a Worthington Diagnostics plate was carried out on additional paired samples of Factor VIII concentrate, using a Biorad water-cooled electrophoresis cell.

Further in vitro experiments were performed by heating lyophilized samples of Factor VIII concentrate in a water bath at room pressure and at predetermined temperatures for predetermined periods of time. Factor $VIII_{Ag}$ was then determined using the method described by Laurell, "Electroimmuno Assay," *The Scandinavian Journal of Clinical and Laboratory Investigation*, Vol. 29, pp. 21–37 (1972). Factor VIII results were calculated for dilutions of 1:40, 1:80, 1:100 and 1:200 by plotting the height of the rockets of the Laurell standard curve against the percentage of dilution. Unknowns were expressed as a percentage of normal, based on the rocket heights of the unknowns in the standard curve.

In vivo recovery of clotting factor activity for both heat-treated Factor VIII and Factor IX concentrates was measured by injecting reconstituted, heat-treated lyophilized Factor VIII and Factor IX concentrates respectively into hemophilia A and hemophilia B dogs. A heat-treated, lyophilized Factor IX concentrate was also injected into a control dog. Laboratory parameters including Hct, serum protein, WBC, platelet count, blood smear, respiration rate, body temperature, pulse and clotting factor activity were subsequently ascertained for each of the animals at various intervals following the injections.

Results of the in vitro testing performed on Factor VIII concentrate are summarized in Tables I and II:

TABLE I

Measurements of Clotting Factor Activity Following Heat-Treatment of Lyophilized Factor VIII Concentrate

| Lot | Temp. | Time | Dilution | % Activity |
|---|---|---|---|---|
| *A C-1081 | Control | — | 1:20 | Approximately |
| " | " | — | 1:40 | 10 % decrease in |
| " | " | — | 1:80 | activity was |
| " | 60° C. | 10 hr. | 1:20 | observed for |
| " | " | " | 1:40 | heat-treated |
| " | " | " | 1:80 | samples relative to the control. |
| A NC-8247 | Control | — | 1:40 | 1438 |
| " | " | — | 1:80 | 1697 |
| " | 62°–64° C. | 16.33 hr. | 1:40 | 1215 |
| " | " | " | 1:80 | 1360 |
| B AHF-355 | Control | — | 1:40 | 1912 |
| " | " | — | 1:80 | 1600 |
| " | " | — | 1:160 | 1312 |
| " | 64° C. | 20 hr. | 1:40 | 1080 |
| " | " | " | 1:80 | 1072 |
| " | 74° C. | 17 hr. | 1:40 | 1144 |
| " | " | " | 1:80 | 1024 |
| " | " | " | 1:160 | 864 |
| " | 76° C. | " | 1:40 | 1040 |
| " | " | " | 1:80 | 976 |
| B 347 | Control | — | 1:100 | 1180 |
| " | " | — | 1:200 | 1000 |
| " | 83° C. | 24 hr. | 1:100 | 100 |
| " | " | " | 1:200 | 100 |
| " | 85° C. | 24 hr. | 1:100 | <1 |
| " | 95° C. | 7 hr. | 1:100 | <1 |
| " | 97° C. | 7.5 hr. | 1:200 | <1 |
| C AL-0470 | Control | — | 1:100 | 912 |
| " | 75° C. | 20 hr. | 1:100 | 2076 |
| C Al-1080 | Control | — | 1:200 | 2080 |
| " | " | " | 1:400 | 1920 |
| " | 80° C.** | 24 hr. | 1:200 | 1380 |
| " | 80° C.** | " | 1:400 | 1360 |
| C Al-1120 | Control | — | 1:40 | 2800 |
| " | " | — | 1:80 | 2032 |
| " | 78° C. | 21 hr. | 1:40 | 1592 |
| " | " | " | 1:80 | 1392 |
| " | 80° C. | 20 hr. | 1:40 | 1176 |
| " | " | " | 1:80 | 1600 |
| " | 90° C. | 12 hr. | — | Clotted Specimen |
| " | 100° C. | 1.5 hr. | 1:40 | 1248 |
| " | " | " | 1:80 | 1264 |
| C Al-1150 | Control | — | 1:40 | 2176 |
| " | " | — | 1:80 | 2480 |
| " | " | — | 1:100 | 1870 |
| " | " | — | 1:200 | 2080 |
| C Al-1150 | 65° C.*** | 26.33 hr. | 1:40 | 1592 |
| " | " | " | 1:80 | 1520 |
| " | 83° C. | 24 hr. | 1:100 | 730 |
| " | " | " | 1:200 | 620 |
| " | 85° C. | 24 hr. | 1:100 | 1000 |
| " | " | " | 1:200 | 1160 |
| " | 90° C. | 10 hr. | 1:40 | 1032 |
| " | " | " | 1:80 | 1056 |
| " | 95° C. | 7 hr. | — | Clotted Specimen |
| " | 97° C. | 7.5 hr. | 1:100 | 80 |
| " | " | " | 1:200 | 100 |
| " | 100° C. | 10 hr. | 1:40 | 88 |
| " | " | " | 1:80 | 48 |
| C Al-1160 | Control | — | 1:100 | 3680 |
| " | " | — | 1:200 | 3420 |
| " | " | — | 1:400 | 3200 |
| " | 78° C. | 24 hr. | 1:100 | 2420 |

TABLE I-continued

Measurements of Clotting Factor Activity Following
Heat-Treatment of Lyophilized Factor VIII Concentrate

| Lot | Temp. | Time | Dilution | % Activity |
|---|---|---|---|---|
| " | " | " | 1:200 | 1520 |
| " | " | " | 1:400 | 1440 |
| " | 78° C. | 24 hr. | 1:200 | 1720 |
| " | " | " | 1:400 | 1680 |
| " | 80° C. | 22 hr. | 1:200 | 1400 |
| " | " | " | 1:400 | 1360 |
| " | 100° C. | 7 hr. | 1:200 | 1760 |
| " | " | " | 1:400 | 1760 |
| C Al-2120 | Control | — | 1:100 | 816 |
| " | 110° C.**** | 1.5 hr. | 1:100 | 18 |
| C Al-2531 | Control | — | 1:200 | 3500 |
| " | " | — | 1:400 | 2700 |
| " | 85° C.***** | 20 hr. | 1:200 | 46 |
| " | 85° C.***** | " | 1:400 | 43 |

Note: All times and temperatures are approximate.
*A lots were manufactured by Cutter Laboratories;
B lots were manufactured by Michigan Department of Health;
C lots were manufactured by Alpha Therapeutics.
**Heat-treated sample remained in a highly viscous state and did not completely solubilize upon initial reconstitution using 25 ml sterile water recommended by manufacturer. Viscosity and solubility of sample both showed marked visual improvement after total of 50 ml sterile water added to sample.
***Heat-treated in a dry oven (sample removed from vial).
****Heat-treated in a dry oven (sample contained in vial).
*****Heat-treated sample remained in a highly viscous state and did not completely solubilize upon initial reconstitution using 25 ml sterile water recommended by manufacturer. Viscosity and solubility of sample both showed marked visual improvement after total of 75 ml sterile water added to sample.

TABLE II

Determination of Factor VIII$_{Ag}$ Following
Heat-Ireatment of Lyophilized Factor VIII Concentrate

| Lot | Temp | Time | Dilution | Rocket Height (mm) | % Ag |
|---|---|---|---|---|---|
| *B AHF-355 | Control | — | 1:40 | 35 | 3720 |
| " | " | — | 1:80 | 22 | 4080 |
| " | 64° C. | 20 hr. | 1:40 | 39 | 4240 |
| " | " | " | 1:80 | 26 | 5120 |
| " | 74° C. | 17 hr. | 1:40 | 40 | 4400 |
| " | " | " | 1:80 | 26 | 5120 |
| C Al-1120 | Control | — | 1:100 | 15 | 4700 |
| " | 90° C. | 12 hr. | 1:100 | 0 | 0 |
| C Al-1150 | Control | — | 1:200 | 13 | 7200 |
| " | 83° C. | 24 hr. | 1:200 | 12 | 6200 |
| " | 85° C. | 24 hr. | 1:200 | 15 | 9400 |
| " | 97° C. | 7.5 hr. | 1:200 | 0 | 0 |

Note: All times and temperatures are approximate. Following heat treatment at higher temperatures, amounts of sterile water in excess of manufacturer's recommendations were added to some concentrates until solubilization was visually confirmed.
*B lots were manufactured by Michigan Department of Health; C lots were manufactured by Alpha Therapeutics.

Results from the testing of Factor IX concentrate are summarized in Table III:

TABLE III

Measurements of Clotting Factor Activity Following
Heat-Treatment of Lyophilized Factor IX Concentrate

| Lot | Temp. | Time | Dilution | % Activity |
|---|---|---|---|---|
| *A 9-C0044 | Control | — | 1:40 | 616 |
| " | " | — | 1:80 | 1200 |
| " | " | — | 1:200 | 2400 |
| " | " | — | 1:400 | 3520 |
| " | 100° C. | 4 hr. | 1:40 | 520 |
| " | " | " | 1:80 | 1104 |
| " | 100° C. | 12 hr. | 1:200 | 1680 |
| " | " | " | 1:400 | 2480 |
| " | 110° C.** | 13 hr. | 1:400 | 1640 |
| " | " | " | 1:800 | 2560 |
| " | 122° C.** | 12 hr. | 1:200 | 340 |
| " | " | " | 1:400 | 480 |
| " | 132° C.** | 12 hr. | 1:200 | 12 |
| " | 132° C.** | " | 1:400 | 24 |
| A NC 9055 | Control | — | n/a | 2600 |

TABLE III-continued

Measurements of Clotting Factor Activity Following
Heat-Treatment of Lyophilized Factor IX Concentrate

| Lot | Temp. | Time | Dilution | % Activity |
|---|---|---|---|---|
| " | 100° C. | 0.5 hr. | n/a | 2350 |

Note: All times and temperatures are approximate. Following heat treatment at higher temperatures, amounts of sterile water in excess of manufacturer's recommendations were added to some concentrates to improve solubility.
A lots manufactured by Cutter Laboratories.
**Heat treated in a dry oven.

Results of the testing performed on fibrinogen concentrate are summarized in Table IV:

TABLE IV

Recovery of Fibrinogen Following Heat-Treatment
of Fibrinogen Concentrate in Lyophilized Form

| Lot | Temp. | Time | Dilution | Recovery (mg/dl) |
|---|---|---|---|---|
| *D-003678 | Control | — | 1:20 | 400 |
| " | " | — | 1:40 | 680 |
| " | 60° C. | 10-11 hr. | 1:20 | 660 |
| " | " | " | 1:40 | 680 |
| " | Control | — | 1:10 | 195 |
| " | " | — | 1:20 | 760 |
| " | " | — | 1:40 | 700 |
| " | 60° C. | 10 hr. | 1:10 | 105 |
| " | " | " | 1:10 | 225 |
| " | " | " | 1:20 | 250 |
| " | 60° C. | 17 hr. | 1:10 | 190 |
| " | " | " | 1:20 | 220 |
| *E | Control | — | 1:40 | 1280 |
| " | " | — | 1:80 | 1280 |
| " | 60° C. | 10 hr. | 1:40 | 1520 |
| " | " | " | 1:80 | 1320 |
| " | 60° C. | 10 hr. | 1:40 | 1860 |
| " | " | " | 1:80 | 1520 |
| " | 65° C. | 10 hr. | 1:40 | 1640 |
| " | " | " | 1:80 | 1400 |
| *E | 65° C. | 23 hr. | 1:40 | 1420 |
| " | " | " | 1:80 | 1320 |
| " | Control | — | 1:40 | 1048 |
| " | " | — | 1:80 | 1064 |
| " | 100° C. | 3 hr. | 1:40 | 788 |
| " | " | " | 1:80 | 784 |
| " | 254° F.** | 3 hr. | 1:5 | 133 |

Note: All times and temperatures are approximate. Following heat treatment at higher temperatures, amounts of sterile water in excess of manufacturer's recommendations were added to some concentrates until complete solubilization was visually confirmed.
D lots manufactured by Cal Biochem; E lots manufactured by Kabi.
*Heat-treated in a dry oven (sample contained in vial).

DISCUSSION OF SELECTED TEST RESULTS

The results summarized in Tables I-IV can be combined to provide a relative indication of clotting activity retention and fibrinogen recovery in lyophilized plasma fractions subjected to the heat-treatment process of the present invention. More particularly, the percentage activity or measured recovery at various dilutions of reconstituted Factor VIII, Factor IX and fibrinogen concentrates can be averaged for individual control samples and compared with similarly-averaged percentage activity or measured recovery in corresponding paired samples of heat-treated Factor VIII, Factor IX and fibrinogen concentrate. Where such comparisons are made, it can be seen, for example, that lyophilized Factor VIII concentrate obtained from one manufacturer (Lot No. A C-1081) and heated at 60° C. for 10 hours retained greater than 90% of its in vitro Factor VIII clotting activity in comparison to an unheated control. The reconstituted, heat-treated Factor VIII concentrate further exhibited an absorbance of 0.30 at 580 nm in comparison to an absorbance of 0.20 for the unheated control, and showed no differences relative to the unheated control following immunoelectrophoresis with the goat anti-human serum. Reconstituted Factor VIII concentrates from a different lot (Lot No. A NC-8247) of the same manufacturer, which had been heated in lyophilized form at 62°–64° C. for approximately 16 hours and then stored at 6° C. for seven days, showed greater than 80% recovery of Factor VIII clotting activity in comparison to an unheated control. An overall increase in anodal migration relative to the unheated control was noted following immunoelectrophoresis against goat anti-human serum.

In similar fashion, lyophilized Factor VIII concentrate obtained from a second manufacturer (Lot No. C Al-1120), when heated at approximately 78° C. for 21 hours, showed 62% in vitro retention of clotting activity upon reconstitution as compared to an unheated control. Reconstituted Factor VIII concentrate from the same lot of the second manufacturer, after heat treatment in lyophilized form for 20 hours at approximately 80° C., still retained 57% in vitro clotting activity as compared to an unheated control, whereas reconstituted Factor VIII from the same lot of the second manufacturer, which had previously been heated in lyophilized form for one and one-half hour at approximately 100° C., retained approximately 52% in vitro clotting activity as compared to an unheated control. When a different lot (Lot No. C Al-1150) of lyophilized Factor VIII concentrate from the second manufacturer was heat-treated in accordance with the present invention, in vitro recoveries of clotting activity in comparison to the unheated control ranged from 67% for 26 hours and 20 minutes of heat treatment at 65° C. to 34% for 24 hours of heat treatment at 83° C. to 55% for 24 hours of heat treatment at 85° C. Measurements of Factor VIII antigen for the two samples of Factor VIII concentrate heat-treated at 83° C. and 85° C. respectively showed a 15% loss and no loss in antigen levels.

Heat treatment of lyophilized Factor VIII samples obtained from a third manufacturer (Lot No. AHF-355) confirmed results observed for the first two manufacturers. That is, heat treatment of the third manufacturer's lyophilized Factor VIII concentrate for 20 hours at 64° C. yielded clotting activity recovery of 61% in comparison to an unheated control, heat treatment of the same concentrate for 17 hours at 74° C. yielded clotting activity recovery of 63% and heat treatment of the same concentrate for 17 hours at 76° C. yielded clotting activity recovery of 57%. Factor VIII antigen levels in the reconstituted samples heated at 64° C. and 74° C. showed no decrease when compared to the unheated control level.

It should be noted that at least two samples of heat-treated Factor VIII concentrate (Lot No. C Al-1080 and Lot No. C Al-2531) were too viscous for use following reconstitution according to manufacturer's specifications. Viscosity of the concentrates was markedly improved and complete solubilization achieved by adding sterile water to the samples in excess of that recommended by the manufacturer.

A sample of lyophilized Factor IX concentrate obtained from the first manufacturer (Lot No. A 9-C0044) and immersed in a water bath at 100° C. for 20–30 minutes yielded essentially full in vitro recovery of clotting activity when compared to an unheated control. Factor II and Factor VII both appeared stable 2 hours following reconstitution of the heat-treated sample, while Factor X decreased approximately 20% within 6 days of reconstitution. Absorbance measurements obtained 2 hours after reconstitution yielded values of 0.006 to 0.007 at 580 mm for both control and heat-treated samples. No visual difference could be detected between the heat-treated concentrate and the unheated control following immunoelectrophoresis of the Factor IX concentrate against goat anti-human serum. Additional samples of Factor IX concentrate from the first manufacturer, which were respectively heat-treated in lyophilized form at 100° C. for 12 hours and at 110° C. for 13 hours, also showed full recovery of Factor IX clotting activity, although solubilization of the latter sample required 40 ml to 60 ml of sterile water as opposed to the manufacturer's recommended 20 ml. The data from Table III thus suggests that Factor IX concentrate in lyophilized form is largely heat stable at temperatures between 100°C.–110° C.

A sample of lyophilized fibrinogen concentrate obtained from a fourth manufacturer (Lot No. D-003678) and heat-treated for 11 hours at 60° C. showed no in vitro loss of fibrinogen when compared with an unheated control. A sample of lyophilized fibrinogen concentrate obtained from the same manufacturer, when heat-treated for 17 hours at 60° C., showed a fibrinogen recovery of 97% compared with the unheated control. Samples of lyophilized fibrinogen concentrates obtained from a fifth manufacturer (Lot E), when heated for 10 and 23 hours respectively at 60° C. and 65° C., showed no in vitro loss of fibrinogen relative to the unheated control, while a sample of lyophilized fibrinogen concentrate from the fifth manufacturer showed 74% fibrinogen recovery compared to the control following heat treatment for 3 hours at 100° C.

As previously indicated, in vivo testing of heat-treated Factor VIII and Factor IX concentrates was carried out using hemophilia A or Factor VIII deficient and hemophilia B or Factor IX deficient dogs. The hemophilia A dog received reconstituted Factor VIII concentrate which had previously been heat-treated in lyophilized form at 60° C. for 10 hours, while the hemophilia B dog received reconstituted Factor IX concentrate which had previously been heat-treated at 100° C. for 3 to 4 houri. Results of the in vivo testing are reported in Tables V and VI below.

TABLE V

| | F-VIII Deficient Dog Given Heat Treated Factor VIII Concentrate | | | | | | | | |
|---|---|---|---|---|---|---|---|---|---|
| | HCT % | Protein gm % | WBC /mm$^3$ | Platelets /mm$^3$ | FVIII RA %° | FVIII C %° | Temp °F. | Respiration | Pulse |
| PRE | 44 | 6.1 | 3,795 | 330,000 | 106 | <2 (1-2) | 100.0 | 48 | 132 |
| Infusion | 20 ml given in 3.5 min | | | | | 400° | | | |
| 15 min | 45 | 5.9 | 3,190 | 110,000 | 151 | 12 | 102.3 | 42 | 138 |
| 90 min | 47 | 6.0 | 6,050 | 165,000 | n = 2 156, 159 | 12 | 101.0 | pant | 108 |
| 3 hours | 44 | 6.1 | 5,115 | 231,000 | 168 | 15 | 100.9 | pant | 108 |
| 5 hours | 43 | 6.0 | 4,785 | 165,000 | 159 | 9 | 100.5 | 30 | 114 |

TABLE V-continued

F-VIII Deficient Dog Given
Heat Treated Factor VIII Concentrate

| | HCT % | Protein gm % | WBC /mm$^3$ | Platelets /mm$^3$ | FVIII RA %° | FVIII C %° | Temp °F. | Respiration | Pulse |
|---|---|---|---|---|---|---|---|---|---|
| 7.5 hours | 44 | 5.9 | 3,245 | 198,000 | 150 | 9 | 101.0 | 42 | 108 |

TABLE VI

F-IX Deficient Dog Given
Heat Treated Factor IX Concentrate

| | HCT % | Protein gm % | WBC /mm$^3$ | Platelets /mm$^3$ | Thrombin clot time sec | FVIII C %° | F-IX %° | Temp °F. | Respiration | Pulse |
|---|---|---|---|---|---|---|---|---|---|---|
| PRE | 43 | 5.5 | 5,840 | 187,000 | 5.5 | 67 | <1 (0-5-1) | 101.5 | 36 | 150 |
| Infusion | | 20 ml given in 3 min. | | | | 5° | 524° | | | |
| 15 min | 42 | 5.6 | 5,005 | 429,000 | 5.5 | 47 | 9 | 101.8 | 30 | 150 |
| 90 min | 44 | 5.8 | 6,545 | 253,000 | 5.5 | 59 | . 10 | 102.0 | 48 | 144 |
| 3 hours | 40 | 5.7 | 8,910 | 429,000 | 6.0 | 39 | 6 | | 42 | 162 |
| 5 hours | 41 | 5.8 | 5,610 | 231,000 | 6.0 | 64 | 6 | 100.3 | 42 | 126 |
| 7.5 hours | 44 | 5.7 | 6,985 | 363,000 | 5.5 | 95 | 4 | 101.0 | 36 | 162 |

The results reported in Table V amply illustrate the marked increase in Factor VIII clotting activity for a hemophilia A dog following injection of heat-treated Factor VIII concentrate. Similarly, the results reported in Table VI amply illustrate the Factor IX recovery observed in a hemophilia B dog following injection of heat-treated Factor IX concentrate. The apparent absence of disseminated intravascular coagulation as seen from the data in Tables V and VI suggests that Factor VIII and Factor IX concentrates which have been processed according to the steps of the present invention remain biologically acceptable.

It has now been demonstrated that plasma fractions such as Factor VIII and Factor IX concentrates of varying purity can be safely heat-treated in lyophilized form at elevated temperatures for extended periods of time without significantly destroying the clotting activity of the concentrates. It has also been demonstrated that plasma fractions such as fibrinogen of varying purity can be safely heat-treated in lyophilized form at elevated temperatures fo extended periods of time without destroying the recoverability of the fibrinogen. Through suitable adjustment of times and temperatures within the ranges reported in Tables I-IV or, alternately, by suitable extrapolation of times and temperatures beyond the ranges reported in Tables I-IV, effective time/temperature combinations can be established for use in heat-treating plasma fractions, whereby the plasma fractions can be safely sterilized. The present invention thus represents a significant advancement in the field of blood technology. This is particularly true with regard to Factor VIII concentrate, which is known to possess a very brief half-life relative to plasma fractions such as fibrinogen. The fragile nature of Factor VIII and its related heat-instability have in the past presented serious impediments to developing hepatitis-free Factor VIII concentrate, even while progress in removing hepatitis virus from other plasma fractions was being made. Use of the method of the present invention, however, overcomes the inherent instability of Factor VIII and furnishes a practical, economic means for providing reduced risk clotting factor concentrates.

Visual observations further confirm that the solubility of lyophilized Factor VIII, Factor IX and fibrinogen concentrates is not deleteriously effected by the high-temperature heat-treatment of the present invention, inasmuch as the amount of diluent added to the lyophilized concentrate samples during reconstitution can be increased until complete solubility is achieved. The latter observation is important from a practical standpoint. Typically, bulk manufacturers of lyophilized clotting factor concentrates and other plasma derivatives instruct end users to carry out resolubilization of the lyophilized concentrates with specified amounts of diluent, e.g., sterile water, saline solution or the like, which specified amounts have been empirically determined to insure adequate solubility of the concentrates upon reconstitution. Where an attempt to resolubilize a heat-treated lyophilized concentrate according to manufacturer's specifications yields a solution of unacceptable viscosity, the addition of an appropriate diluent in excess of that previously thought necessary for solubility, i.e., in excess of that recommended by the manufacturer, will result in complete solubilization of the concentrate without destroying clotting factor activity. The ability to compensate for increased viscosity of concentrates heat-treated over extended periods of time at high temperatures greatly enhances the utility and commercial attractiveness of the present invention. Given the knowledge that lyophilized concentrates which might otherwise be rendered unusable by heat-treatment can nevertheless be recovered, temperatures and heating times for the concentrates can be adjusted upward to the level required for inactivating hepatitis virus of both the B type and the non-A, non-B type present in the concentrates.

It should be apparent upon reflection that the method of the present invention is useful in inactivating or eliminating biological substances other than hepatitis virus which may be present in plasma or plasma derivatives. Heat treatment of lyophilized plasma or plasma derivatives following the process steps outlined above may be employed in connection with CMV virus, viruses associated with Acquired Immune Deficiency Syndrone (commonly known as "AIDS"), Epstein-Barr virus, and like undesirable microorganisms. Moreover, the method of the present invention can be used to treat plasma or plasma derivatives which have been dehydrated by processes other than lyophilization (or freeze-drying), e.g., by processes such as spray drying and vacuum drying. When spray drying and vacuum drying techniques are employed, care should be exercised to insure that the amount of moisture removed from the plasma derivatives during drying is sufficient to render the derivatives heat-stable. Additional care may be required where spray drying or vacuum drying of Factor VIII concentrate is contemplated. Factor VIII is a large and relatively complex molecule, and the procedures associated with spray drying and vacuum drying may unacceptably damage Factor VIII unless special precautions are taken. For this reason, lyophilization or freeze drying is the preferred mode of removing moisture from Factor VIII concentrate prior to heat-treating.

It should also be apparent from extrapolation of the test results reported in Tables I–VI that the method of the present invention can be performed at essentially any point during the plasma fractionation process. That is, at any point along the fractionation process where a plasma or plasma derivative can be lyophilized, heat treatment of the plasma or its derivative can be performed and the plasma or plasma derivative resolubilized or reconstituted prior to continuation of the fractionation process. Thus, for example, where Factor VIII concentrate is ultimately derived from a plasma fractionation scheme such as that disclosed in Mammen, et al., "Treatment of Bleeding Disorders with Blood Components," *Reviews of Hematology*, Vol. 1, p. 144 (1980), whole plasma, cryoprecipitate obtained from fresh frozen plasma, clarified extract obtained from cryoprecipitate and supernatant obtained from clarified extract can all be lyophilized and heat-treated in the same manner as the Factor VIII concentrate itself. Selection of an appropriate point in the plasma fractionation scheme for applying the heat treatment can then be based on progmatic considerations such as cost or convenience.

Finally, and in recognition of the fact that hepatitis B virus and probably non-A, non-B hepatitis are distributed in the clotting factor derivatives, i.e., in Factor VIII and Factor IX concentrates, heat treatment of clotting factor fractions in lyophilized or dried form at suitable temperatures for suitable periods of time can serve to render hepatitis virus present in the concentrates immunogenic as well as non-infectious. Consequently, reconstituted heat-treated lyophilized Factor VIII and Factor IX concentrates can function as hepatitis vaccines while simultaneously providing the therapeutic benefits normally associated with clotting factor fractions.

Several embodiments of the present invention have been illustrated hereinabove. It is to be understood, however, that various modifications to the temperature ranges, heating periods and purity levels set forth in conjunction with the aforementioned embodiments can be made by those skilled in the art without departing from the scope and spirit of the present invention. It is therefore the intention of the inventor to be bounded only by the limits of the following claims.

What is claimed is:

1. A method of treating human blood clotting Factor VIII concentrate in order to minimize the effect of undesirable virus microorganisms present in said human blood clotting Factor VIII concentrate, said method comprising the steps of:
   lyophilizing said human blood clotting Factor VIII concentrate;
   heating said lyophilized human blood clotting Factor VIII concentrate at a predetermined temperature of at least about 60° C. for a period of time sufficient to minimize the effect of any undesirable virus microorganisms present in said human blood clotting Factor VIII concentrate, said heating generally decreasing as said predetermined temperature is increased.

2. The method claimed in claim 1 wherein said predetermined temperature is between about 60° C. and about 100° C.

3. The method claimed in claim 1 wherein said predetermined temperature is between about 100° C. and about 125° C.

4. A method of treating human blood clotting Factor VIII concentrate in order to minimize the effect of undesirable virus microorganisms present in said human blood clotting Factor VIII concentrate, said method comprising the steps of:
   dehydrating said human blood clotting Factor VIII concentrate;
   heating said dehydrated human blood clotting Factor VIII concentrate at a predetermined temperature of at least about 60° C. for a period of time sufficient to minimize the effect of any undesirable virus microorganisms present in said human blood clotting Factor VIII concentrate, said heating generally decreasing as said predetermined temperature is increased.

5. A method of treating human blood clotting Factor VIII concentrate in order to minimize the effect of AIDS virus microorganisms present in said blood clotting Factor VIII concentrate, said method comprising the steps of:
   lyophilizing said blood clotting Factor VIII concentrate;
   heating said blood clotting Factor VIII concentrate for a predetermined period of time at a predetermined temperature of at least about 60° to inactivate AIDS microorganisms in said blood clotting Factor VIII concentrate said heating time generally decreasing as said temperature is increased.

6. A method of treating human blood clotting Factor VIII concentrate in order to minimize the effect of CMV virus microorganisms present in said blood clotting Factor VIII concentrate, said method comprising the steps of:
   lyophilizing said blood clotting Factor VIII concentrate;
   heating said blood clotting Factor VIII concentrate for a predetermined period of time at a predetermined temperature of at least about 60° C. to inactivate CMV microorganisms in said blood clotting Factor VIII concentrate, said heating time generally decreasing as said temperature is increased.

7. A method of treating human blood clotting Factor VIII concentrate in order to minimize the effect of Epstein-Barr virus microorganisms present in said blood clotting Factor VIII concentrate, said method comprising the steps of:
   lyophilizing said blood clotting Factor VIII concentrate;
   heating said blood clotting Factor VIII concentrate for a predetermined period of time at a predetermined temperature of at least about 60° C. to inactivate Epstein-Barr microorganisms in said blood clotting Factor VIII concentrate, said heating time generally decreasing as said temperature is increased.

8. A method of treating blood clotting Factor VIII concentrate in order to minimize the effect of undesirable virus microorganisms present in said blood clotting Factor VIII concentrate, said method comprising the steps of:

lyophilizing said blood clotting Factor VIII concentrate;

heating said blood clotting Factor VIII concentrate for a predetermined period of time at a predetermined temperature of at least about 60° C. to inactivate any undesirable microorganisms in said blood clotting Factor VIII concentrate, said heating time generally decreasing as said temperature is increased; and reconstituting the heated lyophilized blood clotting Factor VIII by increasing the moisture content thereof to a predetermined level irrespective of the amount of moisture removed when lyophilizing the blood clotting Factor VIII, said predetermined level being sufficient to completely solubilize the heated, lyophilized blood clotting Factor VIII.

9. A human blood clotting Factor VIII concentrate, said human blood clotting Factor VIII concentrate having been treated to minimize the effect of undesirable virus microorganisms by lyophilizing said human blood clotting Factor VIII concentrate followed by heating at a predetermined temperature of at least about 60° C. for a period time sufficient to minimize the effect of any undesirable virus microorganisms.

10. The human blood clotting Factor VIII concentrate claimed in claim 9 wherein said undesirable virus microorganisms are further defined as AIDS virus.

11. The human blood clotting Factor VIII concentrate claimed in claim 9 wherein said undesirable virus microorganisms are further defined as CMV virus.

12. The human blood clotting Factor VIII concentrate claimed in claim 9 wherein said undesirable virus microorganisms are further defined as Epstein-Barr virus.

* * * * *

REEXAMINATION CERTIFICATE (1098th)
United States Patent [19]
Rubinstein

[11] B1 4,556,558
[45] Certificate Issued * Jul. 11, 1989

[54] TREATMENT OF FACTOR VIII CONCENTRATE TO MINIMIZE THE AFFECT OF UNDESIRABLE MICROORGANISMS

[75] Inventor: Alan Rubinstein, Beverly Hills, Calif.

[73] Assignee: Cedars-Sinai Medical Center, Los Angeles, Calif.

Reexamination Reqs:st:
No. 90/001,295, Jul. 31, 1987
No. 90/001,412, Jan. 15, 1988
No. 90/001,454, Feb. 29, 1988
No. 90/001,590, Sep. 2, 1988

Reexamination Certificate for:
Patent No.: 4,556,558
Issued: Dec. 3, 1985
Appl. No.: 624,992
Filed: Jun. 26, 1984

[*] Notice: The portion of the term of this patent subsequent to Jun. 26, 2001 has been disclaimed.

Related U.S. Application Data

[63] Continuation of Ser. No. 499,489, May 31, 1983, abandoned, which is a continuation-in-part of Ser. No. 377,863, May 13, 1982, Pat. No. 4,456,590, which is a continuation-in-part of Ser. No. 317,513, Nov. 2, 1981, abandoned, which is a continuation of Ser. No. 205,913, Nov. 12, 1980, abandoned.

[51] Int. Cl.$^4$ .............................................. A61K 37/02
[52] U.S. Cl. ........................................ 514/2; 424/101
[58] Field of Search .............................. 424/101; 514/2

[56] References Cited

U.S. PATENT DOCUMENTS

4,297,344  4/1980  Schwinn et al.
4,327,086  3/1981  Fukushima et al.
4,495,278  4/1981  Thomas.

FOREIGN PATENT DOCUMENTS

59018  11/1976  Japan.

OTHER PUBLICATIONS

Rozenburg et al, "Hemostatic Human Blood Fractions for Transfusion: Antihemophilia Plasma, Antihemophiliac Globulin, and Fibrinogen", Problemy Gematologi i Perelivaniya Krovi, vol. 8, No. 6, pp. 3–6 (1963), (Translation enclosed herewith from "Translation Supplement", Federation Proceedings), vol. 23, No. 2 Part II, pp. T322-T325 (1964).
Abstracts distributed at the XIV Congress of the World Federation of Hemophilia held in Costa Rica in Jul. 3–7, 1981: A. Rubinstein, *Heated Lyophilized Factor VIII Concentrates, Preliminary Studies*, Paper No. FC-5; *Heated Lyophilized Factor VIII Concentrate–Additional in Vitro Studies*, Paper No. FC-6; *Heated Lyophilized Factor IX Concentrate in Vitro Studies*, Paper No. FC-4. A. Rubinstein, *Heated Lyophilized Factor VIII Concentrate–Additional Preliminary in Vitro Studies*, Thrombosis and Haemostasis (ABST), 46:(1), Abst. No. 1051, p. 338 (1981); A. Rubinstein, *Heated Lyopilized Factor VIII and Factor IX Concentrate–Preliminary in Vitro Studies*, Thrombosis and Haemostasis (ABST), 46:(1), Abst. No. 1054, p. 339 (1981).
A. Rubinstein, *Heated Lyophilized Factor VIII Concentrate and Factor IX Concentrate Studies in Hemophilia A and B Dogs*, Blood, vol. 58, No. 5, Abst. No. 650, p. 185a, Suppl. 1 (1981).
G. M. Thelin, *Preparation and Standardization of a Stable AHF Plasma*, Thromb. Diathes. Haemmorh., vol. 19, pp. 423–429 (1968).
D. R. Bangham et al., *Stability of Some Clotting Factors in Freeze-dried Factor VIII-Reference Plasma and Concentrate*, In: Hemophilia Research, Clinical and Psycho-Social Aspects, VI Congress of the World Federation of Haemophilia held in Baden, Austria in Jul. 25th-27th, 1970, Ed. by E. Deutsch and H. W. Pilgerstorfer, pp. 89–98 (1970).
M. V. Podolsky, N. G. Karlova and G. Y. Rosenberg, *Improved Method of Lyophilization of Plasma Stabilized With Glucose*, Problems of Hematology and Blood Transfusion, vol. 4, pp. 27–32 (1967).
E. Bidwell, *The Purification of Bovine Antihaemophilic Globulin*, Br. J. Haematol., vol. 1, pp. 35–45 (1955).
Thomas, U.S. Patent No. 4,495,278.
G. Y. Rosenberg, A. E. Kiselev, L. F. Barinsky, M. A. Blinova and G. V. Khailo, *On the Thermoinactivation of Botkin's Hepatitis Virus in Dry Fibrinogen and Albumin Preparations*, Proc. 12th Int. Soc. Blood Transf., Moscow, 1969, Bibl. Haemat., No. 38, part II, pp. 474–478 (Karger, Basel 1971).
Rosenberg et al, "On the Thermoinactivation of Botkin's Hepatitis Virus in Dry Fibrinogen and Albumin Preparations", Proc 12th Congr. Int. Soc. Blood Transf., Moscow, 1969, Bibl. Haemat., No. 38, Part II, pp. 474–478 (Karger, Basel 1971).
E. Bidwell et al, "Therapeutic Materials", Human Blood Coagulation, pp. 262, 274 (Biggs, ed, 2nd ed, Oxford: Blackwell Scientific Publications, Philadelphia, Lippincott, (1976).
I. M. Nilsson et al, "Characteristics of the Factor VIII Protein and Factor XIII in Various Factor VIII Concentrates," Scand J Haematol (1980) 24, 340–349.
Podolsky et al, "Improved Method of Lyophylic Desiccation of Glucose Stabilized Plasma", Problems of Hematology and Blood Transfusion, 4, pp. 27–32 (1967).
Bangham et al, "A Biological Standard for Measurement of Blood Coagulation Factor VIII Activity," Bulletin of the World Health Organization, vol. 45, No. 3, 337–351, (1971).
F. Feldman, "New Developments in F VIII Purification, An Overview," Bloodtransfusion and Problems of Bleeding, Symposium on Blood Transfusion (6th: 1981 Groningen, Netherlands).
Aronson et al, "Historical and Future Therapeutic Plasma Derivatives", Seminars in Thrombosis and Hemostasis, vol. VI, No. 2, (1980), p. 123.

Gerety et al, "Plasma Derivatives and Viral Hepatitis", Transfusion, vol. 22, No. 5, Sep.-Oct. 1982, p. 347.

Tabor, Infectious Complications of Blood Transfusion, p. 6, (Academic, 1982).

Plasma Products: Use and Management A Technical Workshop (1982), Kolins et al, editors, p. 6.

J. Sonnabend et al, JAMA, vol. 249, No. 17, p. 2370 (1983).

J. L. Marx, "New Disease Baffles Medical Community," Science, vol. 217, No. 4560, Aug. 13, 1982, pp. 618–621.

Epidemiologic Notes and Reports, "Penumocystis carinii Pneumonia among Persons with Hemophilia A," MMWR, Jul. 16, 1982, vol. 31, No. 27, pp. 365-367.

Epidermiologic Notes and Reports, "Update on Acquired Immune Deficiency Syndrome (AIDS) among Patients with Hemophilia A," MMWR, vol. 31, No. 48, Dec. 10, 1982, pp. 644–654.

"Current Trends, Prevention of Acquired Immune Deficiency Syndrome (AIDS): Report of Inter-Agency Recommendations," MMWR, vol. 32, No. 8, Mar. 4, 1983, pp. 101–103.

Petricciani et al, The Lancet, Oct. 19, 1985.

S. M. Feinsteone et al, "Transfusion-Associated Hepatitis Not Due to Viral Hepatitis Type A or B", N Engl J. Med., vol. 292, pp. 767-770 (1974).

R. L. Cavenaugh, "Cytomegalovirus and the Post–Transfusion Syndrome", Maryland State Medical Journal, pp. 103–104 (Apr., 1970).

"The Several Viruses of Post-Transfusion Hepatitis", British Medical Journal, p. 663 (Sep. 20, 1975).

P. Gerber, "EB Herpes Virus", Manual of Clinical Microbiology, third ed., Lennette editor-in-chief, p. 807 (1980).

R. D. Krugman et al, "Human cytomegalovirus, Thermal Inactivation", Virology, vol. 23, pp. 290-291 (1964).

R. S. Chang et al, "In Vitro Stimulation of Lymphocytes of Donors Seronegative Epstein-Barr Virus," The Journal of Infectious Diseases, vol. 133, No. 6, pp. 676–680 (Jun. 1976).

*Primary Examiner*—Sam Rosen

[57] ABSTRACT

The invention is directed to treating blood clotting Factor VIII products to minimize the presence of undesirable microorganisms involving process steps of drying and heating of the product. In addition the invention is directed to products obtained by the process.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 5-7 is confirmed.

Claims 1, 4 and 8-12 are determined to be patentable as amended.

Claims 2 and 3, dependent on an amended claim, are determined to be patentable.

1. A method of treating human blood clotting Factor VIII concentrate in order to minimize the effect of undesirable virus microorganisms *selected from the group consisting of AIDS virus, CMV virus and Epstein-Barr virus* present in said human blood clotting Factor VIII concentrate, said method comprising the steps of:
    lyophilizing said human blood clotting Factor VIII concentrate;
    heating said lyophilized human blood clotting Factor VIII concentrate at a predetermined temperature of at least about 60° C. for a period of time sufficient to minimize the effect of any undesirable virus microorganisms *selected from the group consisting of AIDS virus, CMV virus and Epstein-Barr virus* present in said human blood clotting Factor VIII concentrate, said heating generally decreasing as said predetermined temperature is increased.

4. A method of treating human blood clotting Factor VIII concentrate in order to minimize the effect of undesirable virus microorganisms *selected from the group consisting of AIDS virus, CMV virus and Epstein Barr virus* present in said human blood clotting Factor VIII concentrate, said method comprising the steps of:
    dehydrating said human blood clotting Factor VIII concentrate;
    heating said dehydrated human blood clotting Factor VIII concentrate at a predetermined temperature of at least about 60° C. for a period of time sufficient to minimize the effect of any undesirable virus microorganisms *selected from the group consisting of AIDS virus, CMV virus and Epstein Barr virus* present in said human blood clotting Factor VIII concentrate, said heating generally decreasing as said predetermined temperature is increased.

8. A method of treating blood clotting Factor VIII concentrate in order to minimize the effect of undesirable virus microorganisms *selected from the group consisting of AIDS virus, CMV virus and Epstein-Barr virus* present in said blood clotting Factor VIII concentrate, said method comprising the steps of:
    lyophilizing said blood clotting Factor VIII concentrate;
    heating said blood clotting Factor VIII concentrate for a predetermined period of time at a predetermined temperature of at least about 60° C. to inactivate any undesirable microorganisms *selected from the group consisting of AIDS virus, CMV virus and Epstein-Barr virus* in said blood clotting Factor VIII concentrate, said heating time generally decreasing as said temperature is increased; and reconstituting the heated lyophilized blood clotting Factor VIII by increasing the moisture content thereof to a predetermined level irrespective of the amount of moisture removed when lyophilizing the blood clotting Factor VIII, said predetermined level being sufficient to completely solubilize the heated, lyophilized blood clotting Factor VIII.

9. A human blood clotting Factor VIII concentrate, said human blood clotting Factor VIII concentrate having been treated to minimize the effect of undesirable virus microorganisms *present in said human blood clotting Factor VIII concentrate* by lyophilizing said human blood clotting Factor VIII concentrate followed by heating at a predetermined temperature of at least about 60° C. for a period *of* time sufficient to minimize the effect of any undesirable virus microorganisms.

10. *A* [The] human blood clotting Factor VIII concentrate, *said human blood clotting Factor VIII concentrate having been treated to minimize the effect of undesirable AIDS virus microorganisms by lyophilizing said human blood clotting Factor VIII concentrate followed by heating at a predetermined temperature of at least about 60° C. for a period time sufficient to minimize the effect of any undesirable AIDS virus microorganisms* [claimed in claim 9 wherein said undesirable virus microorganisms are further defined as AIDS virus].

11. *A* [The] human blood clotting Factor VIII concentrate, *said human blood clotting Factor VIII concentrate having been treated to minimize the effect of undesirable CMV virus microorganisms by lyophilizing said human blood clotting Factor VIII concentrate followed by heating at a predetermined temperature of at least about 60° C. for a period time sufficient to minimize the effect of any undesirable CMV virus microorganisms* [claimed in claim 9 wherein said undesirable virus microorganisms are further defined as CMV virus].

12. *A* [The] human blood clotting Factor VIII concentrate, *said human blood clotting Factor VIII concentrate having been treated to minimize the effect of undesirable Epstein-Barr virus microorganisms by lyophilizing said human blood clotting Factor VIII concentrate followed by heating at a predetermined temperature of at least about 60° C. for a period of time sufficient to minimize the effect of any undesirable Epstein-Barr virus microorganisms* [claimed in claim 9 wherein said undesirable virus microorganisms are further defined as Epstein-Barr virus].

* * * * *